(12) United States Patent
Takanashi et al.

(10) Patent No.: US 12,414,558 B2
(45) Date of Patent: Sep. 16, 2025

(54) METHOD FOR ADMINISTERING UMBILICAL CORD BLOOD OR PERIPHERAL BLOOD

(71) Applicants: JAPANESE RED CROSS SOCIETY, Tokyo (JP); ZENOGEN PHARMA CO., LTD., Fukushima (JP)

(72) Inventors: Minoko Takanashi, Tokyo (JP); Miyuki Ito, Tokyo (JP); Kohichi Saze, Fukushima (JP)

(73) Assignees: JAPANESE RED CROSS SOCIETY, Tokyo (JP); ZENOGEN PHARMA CO., LTD., Fukushima (JP)

( * ) Notice: Subject to any disclaimer, the term of this patent is extended or adjusted under 35 U.S.C. 154(b) by 0 days.

(21) Appl. No.: 18/107,320

(22) Filed: Feb. 8, 2023

(65) Prior Publication Data
US 2023/0180740 A1   Jun. 15, 2023

Related U.S. Application Data

(63) Continuation of application No. 15/526,175, filed as application No. PCT/JP2015/082034 on Nov. 13, 2015, now abandoned.

(30) Foreign Application Priority Data

Nov. 14, 2014   (JP) .................................. 2014-232211
Jun. 16, 2015   (JP) .................................. 2015-121460

(51) Int. Cl.
*A01N 1/125* (2025.01)
*A01N 1/162* (2025.01)
*A61K 35/14* (2015.01)
*A61K 35/51* (2015.01)
*C12N 5/078* (2010.01)

(52) U.S. Cl.
CPC ............. *A01N 1/125* (2025.01); *A01N 1/162* (2025.01); *A61K 35/14* (2013.01); *A61K 35/51* (2013.01); *C12N 5/0634* (2013.01)

(58) Field of Classification Search
CPC .... A01N 1/0221; A01N 1/0284; A61K 35/14; A61K 35/51; C12N 5/0634; A61P 7/00; A61P 7/06
See application file for complete search history.

(56) References Cited

U.S. PATENT DOCUMENTS

| | | |
|---|---|---|
| 6,869,758 B1 | 3/2005 | Gao |
| 2004/0241183 A1 | 12/2004 | Hasumi |
| 2005/0026133 A1 | 2/2005 | Nakatsuji |
| 2006/0188984 A1 | 8/2006 | Rudd |
| 2006/0193839 A1 | 8/2006 | Rudd |
| 2009/0104650 A1 | 4/2009 | Walton |
| 2009/0142830 A1 | 6/2009 | Yamashiro et al. |
| 2013/0095079 A1 * | 4/2013 | Bernstein ............... A61K 35/50 435/372 |
| 2013/0280805 A1 | 10/2013 | Pogue et al. |
| 2015/0320031 A1 | 11/2015 | Andreasen |
| 2016/0008408 A1 | 1/2016 | Imagawa et al. |
| 2019/0000070 A1 * | 1/2019 | De Larichaudy ...... A61K 47/20 |

FOREIGN PATENT DOCUMENTS

| | | | |
|---|---|---|---|
| CA | 2597963 | 2/2009 | |
| JP | 2008-237136 | 10/2008 | |
| JP | 2014-113166 | 6/2014 | |
| JP | 2015-142559 | 8/2015 | |
| JP | 2016-501873 | 1/2016 | |
| KR | 10-0953400 | 4/2010 | |
| WO | 9300807 | 1/1993 | |
| WO | 2006/130812 | 12/2006 | |
| WO | WO-2014053420 A1 * | 4/2014 | ............ A61K 35/28 |
| WO | 2014/142038 | 9/2014 | |
| WO | 2015/062267 | 5/2015 | |
| WO | 2015/150394 | 10/2015 | |

OTHER PUBLICATIONS

Djerassi, I et al. Preparation and in vivo circulation of human platelets preserved with combined dimethylsulfoxide and dextrose. Transfusion. 1966. 6(6): 572-576. (Year: 1966).*
Balci, D et al. The assessment of cryopreservation conditions for human umbilical cord stroma-derived mesenchymal stem cells towards a potential use for stem cell banking. Current Stem Cell Research & Therapy. Jan. 2013. 8: 60-72. (Year: 2013).*
Holm, F et al. An effective serum- and xeno-free chemically defined freezing procedure for human embryonic and induced pluripotent stem cells. Human Reproduction. 2010. 25(5): 1271-1279. (Year: 2010).*
International preliminary report on patentability of PCT/JP2015/082034, mailed May 16, 2017, 9 pages.
Takanashi et al. "Red blood cell depletion of cord blood using an automated system—Evaluation of the AXP system." Japanese Journal of Transfusion and Cell Therapy, vol. 56, No. 1 56(1):62-67, 2010.
Ito Miyuki et al. P1-3 Evaluation of a New Cryoprotectant; "Improved Stem-Cellbanker" Programs and Abstracts for the 37th Annual Meeting of the Japan Society for Hematopoietic Cell Transplantation, p. 243, Feb. 2015.

(Continued)

*Primary Examiner* — David W Berke-Schlessel
*Assistant Examiner* — Susan E. Fernandez
(74) *Attorney, Agent, or Firm* — Casimir Jones, S.C.; Robert A. Goetz

(57) ABSTRACT

An object of the present invention is to provide (i) a cryopreservation solution which can be used for cryopreserving umbilical cord blood, peripheral blood, and a component containing hematopoietic stem cells derived from any one of these types of blood and which has characteristics suitable for various utilization forms and (ii) use of the cryopreservation solution. In a cryopreservation method in accordance with the present invention, a cryopreservation solution containing a cryoprotectant and glucose is mixed with umbilical cord blood or peripheral blood, and a mixture thus obtained is frozen.

7 Claims, No Drawings

(56) References Cited

OTHER PUBLICATIONS

Ito Miyuki et al. P1-133 Concentration of Dimethylsulfoxide to Be Used for Cord Blood Cryopreservation, Programs and Abstracts for the 35th Annual Meeting of the Japan Society for Hematopoietic Cell Transplantation, p. 250, Feb. 2013.
Yamaguchi R, Takanashi M, Ito M, et al. "Plasticizer concentration in cord blood cryopreserved with DMSO" Bone Marrow Transplantation, vol. 49, pp. 157-158, 2014.
International Search Report for PCT/JP2015/082034, mailed Jan. 26, 2016, 2 pages.
Holm, F. et al: "An effective serum- and xeno-free chemically defined freezing procedure for human embryonic and induced pluripotent stem cells", Human Reproduction, vol. 25, No. 5, Mar. 5, 2010 Mar. 5, 2010), pp. 1271-1279, XP055412603, GB ISSN: 0268-1161.
EP Search Report, EP Patent Application No. 15859595.9, mailed Oct. 13, 2017.
Office Action, JP Patent Application No. 2016-559123, mailed Jan. 23, 2018.
Quan, GB et al. Effects of pre-freeze incubation of human red blood cells with various sugars on posthaw recovery when using a dextran-rapid cooling protocol. Cyrobiology, 2009. 59: 258-267.
Rodrigues, JP et al. Evaluation of trehalose and sucrose as cryoprotectants for hermatopoietic stem cells of umilibilical cord blood. Cryobiology. 2008. 56: 144-151.
Clark, P et al. Factors influencing renal cryopreservation. II. Toxic effects of three cryoprotectants in combination with three vehicle solutions in nonfrozen rabbit cortical slices. Cryobiology. 1984. 21: 274-284.
Requirement for Restriction / Election, U.S. Appl. No. 15/526,175, mailed Nov. 2, 2018.
Non-Final Rejection, US Patent Application No. 15/526, 175, mailed Mar. 7, 2019, available in PAIR.
Final Rejection, U.S. Appl. No. 15/526,175, mailed Sep. 3, 2019.
Non-Final Rejection, U.S. Appl. No. 15/526,175, mailed Apr. 6, 2020.
Non-Final Rejection, U.S. Appl. No. 15/526,175, mailed Oct. 5, 2020.
Final Rejection, U.S. Appl. No. 15/526,175, mailed Jul. 6, 2021.
Non-Final Rejection, U.S. Appl. No. 15/526,175, mailed Mar. 31, 2022.
Final Rejection, U.S. Appl. No. 15/526,175, mailed Nov. 14, 2022.

* cited by examiner

METHOD FOR ADMINISTERING UMBILICAL CORD BLOOD OR PERIPHERAL BLOOD

This application is a continuation of U.S. patent application Ser. No. 15/526,175, filed May 11, 2017, which is a 371 National Entry Application of PCT/JP2015/082034, filed Nov. 13, 2015, which claims priority to expired Japanese Patent Application No. 2015-121460, filed Jun. 16, 2015, and expired Japanese Patent Application Serial No. 2014-232211, filed Nov. 14, 2014, the contents of which are herein incorporated by reference in their entireties.

TECHNICAL FIELD

The present invention relates to a cryopreservation method and a cryopreservation solution for cryopreserving umbilical cord blood and peripheral blood. More specifically, the present invention relates to a cryopreservation method and a cryopreservation solution for cryopreserving umbilical cord blood and peripheral blood which method and solution allow thawed umbilical cord blood or peripheral blood to have good cell viability and also allow the thawed umbilical cord blood or peripheral blood to be applied safely to a living body.

BACKGROUND ART

Umbilical cord blood and peripheral blood, each of which contains hematopoietic stem cells, have been clinically applied as sources for hematopoietic stem cells, as well as bone marrow. From each of umbilical cord blood and peripheral blood, a component containing hematopoietic stem cells is separated and recovered, if necessary, and then is mixed with a cryopreservation solution and cryopreserved until being used.

Examples of the cryopreservation solution for cryopreserving the component containing the hematopoietic stem cells encompass CP-1 (product name) or CryoSure-DEX40 (product name) (Non-patent Literatures 1 and 2). CP-1 contains hydroxyethylstarch and dimethyl sulfoxide as main components, and CryoSure-DEX40 contains dextran and dimethyl sulfoxide as main components.

CITATION LIST

Non-Patent Literature

[Non-patent Literature 1]
Takanashi M, Oba A, Ogawa A, et al. Red blood cells depletion of umbilical cord blood using an automated system —Evaluation of the AXP system. Japanese Journal of Transfusion and Cell Therapy 56 (1): 62-67, 2010.
[Non-patent Literature 2]
Yamaguchi R, Takanashi M, Ito M, et al. Plasticizer concentration in umbilical cord blood cryopreserved with DMSO. Bone Marrow Transplant 49 (1): 157-8, 2014.

SUMMARY OF INVENTION

Technical Problem

After the cryopreserved component containing the hematopoietic stem cells is thawed, the component is utilized, for example, in such a manner that the hematopoietic stem cells are separated and recovered so as to be used, or in such a manner that the component itself, together with the cryopreservation solution, is applied to a living body. As such, there is a great demand that a cryopreservation solution for umbilical cord blood or peripheral blood, and a cryopreservation solution for a component containing hematopoietic stem cells derived from umbilical cord blood or peripheral blood, have characteristics suitable for various utilization forms.

In relation to application to a living body, hydroxyethylstarch and dextran, which are described in Non-patent Literatures 1 and 2, are components approved as drugs for medical use and are highly safe for a living body when administered to a blood vessel of the living body. However, these components have been reported to have side effects such as anaphylactic shock, and there is a demand for a safer component to be utilized.

Further, in a case where hematopoietic stem cells are separated and recovered from a thawed component so as to be used, a cryoprotective solution is expected to have a composition that allows the hematopoietic stem cells to be easily recovered.

Further, in regard to CP-1, it is essential to add serum album to CP-1 in a standard method of using CP-1. As such, especially for use in medical situations, CP-1 still has room for improvement in terms of ease and speed in handling of CP-1.

The present invention is accomplished in order to solve the foregoing problems. An object of the present invention is to provide (i) a cryopreservation solution which can be used for cryopreserving umbilical cord blood, peripheral blood, and a component containing hematopoietic stem cells derived from any one of these types of blood and which has characteristics suitable for various utilization forms and (ii) use of the cryopreservation solution.

Solution to Problem

A cryopreservation method in accordance with the present invention is a cryopreservation method for cryopreserving umbilical cord blood or peripheral blood, including: a mixing step of mixing a cryopreservation solution with umbilical cord blood or peripheral blood, the cryopreservation solution containing a cryoprotectant and glucose; and a freezing step of freezing a mixture obtained in the mixing step.

A production method in accordance with the present invention for producing frozen umbilical cord blood or frozen peripheral blood is a production method for producing frozen umbilical cord blood or frozen peripheral blood, including: a mixing step of mixing a cryopreservation solution with umbilical cord blood or peripheral blood, the cryopreservation solution containing a cryoprotectant and glucose, the umbilical cord blood or peripheral blood containing living cells; and a freezing step of freezing a mixture obtained in the mixing step.

The present invention also provides frozen umbilical cord blood or frozen peripheral blood, produced by the production method above.

A cryopreservation solution in accordance with the present invention for cryopreserving umbilical cord blood or peripheral blood contains a cryoprotectant and glucose.

A kit in accordance with the present invention is a kit for cryopreserving umbilical cord blood or peripheral blood, including: the cryopreservation solution above for cryopreserving umbilical cord blood or peripheral blood; and a container which is cold resistant and capable of containing (i) the cryopreservation solution and (ii) umbilical cord blood or peripheral blood.

Advantageous Effects of Invention

The use of a cryopreservation method and a cryopreservation solution in accordance with the present invention allows thawed umbilical cord blood or peripheral blood to have good cell viability and also allow the thawed umbilical cord blood or peripheral blood to be applied safely to a living body.

DESCRIPTION OF EMBODIMENTS

As a result of diligent study for attaining the object, the inventors of the present invention have found that, in a case where umbilical cord blood is mixed with a solution containing a cryoprotectant and glucose, and a resultant mixture is frozen, the mixture when thawed has good cell viability. Through this finding, the inventors of the present invention have accomplished the present invention. The following description will discuss embodiments of the present invention in detail.

[Method for Cryopreserving Umbilical Cord Blood or Peripheral Blood]

A cryopreservation method in accordance with the present invention for cryopreserving umbilical cord blood or peripheral blood includes: a mixing step of mixing a cryopreservation solution with umbilical cord blood or peripheral blood, the cryopreservation solution containing a cryoprotectant and glucose; and a freezing step of freezing a mixture obtained in the mixing step.

Umbilical cord blood applicable to the cryopreservation method in accordance with the present invention is not limited to a particular origin, and it is possible to preserve umbilical cord blood of placental mammals in general. Examples of the placental mammals encompass: experimental animals such as mice, rats, rabbits, guinea pigs, and primates other than humans; pets such as dogs and cats; farm animals such as bovines, horses, pigs, and ovines; and humans. Further, peripheral blood applicable to the cryopreservation method in accordance with the present invention is not limited to a particular origin, and may be, for example, any of the animals mentioned above. The cryopreservation method in accordance with the present invention is effectively applicable to human umbilical cord blood and peripheral blood.

Umbilical cord blood may be obtained, for example, by puncturing an umbilical vein and collecting the umbilical cord blood falling freely therefrom. Peripheral blood may be collected, for example, directly by extracorporeal circulation. As such, an embodiment of the cryopreservation method in accordance with the present invention further includes a step of collecting umbilical cord blood from an umbilical cord or a step of collecting peripheral blood from a living body.

The cryoprotectant contained in the cryopreservation solution is not particularly limited, provided that the cryoprotectant can constitute a cryopreservation solution that is capable of sufficiently preserving umbilical cord blood or peripheral blood. Examples of the cryoprotectant can encompass dimethyl sulfoxide (hereinafter, DMSO), glycerol, propylene glycol, 1-methyl-2-pyrolidone, and the like. The cryoprotectant is preferably DMSO or propylene glycol, and particularly preferably DMSO. The content of the cryoprotectant in the mixture obtained in the mixing step is preferably 3.0 w/v % to 10.0 w/v %, more preferably 5.0 w/v % to 8.0 w/v % or 5.0 v/v % to 8.0 v/v %, and from a viewpoint of cell recovery rate and reduction in the amount of DMSO, more preferably 5.0 v/v %.

The content of the glucose in the mixture obtained in the mixing step is preferably 0.25 w/v % to 5.0 w/v %, more preferably 0.5 w/v % to 5.0 w/v %, further more preferably 1.0 w/v % to 2.5 w/v %, and particularly preferably 1.5 w/v % to 2.0 w/v %.

In the cryopreservation solution, the ratio of concentration between the cryoprotectant and the glucose is preferably 20:1 to 1:1, more preferably 10:1 to 2:1, and further more preferably 20:3 to 10:3. This arrangement allows for a significant reduction in concentration of the cryoprotectant as compared with the conventional technique. Accordingly, particularly in a case where the cryopreservation solution is applied to a living body, the cryopreservation solution is safer due to a reduction in the amount of the cryoprotectant entering the living body.

The cryopreservation solution may further contain another component. Examples of the another component can encompass a pH adjusting agent, a thickener, and the like. Examples of the pH adjusting agent can encompass sodium hydrogencarbonate, HEPES, a phosphate buffer solution, and the like. Also, in a case where a basic stock solution (BSS) does not contain phosphate buffer solution, one added with physiological saline can also be used. Among these components, it is particularly preferable to use the phosphate buffer solution. It is preferable that the pH adjusting agent be used as appropriate in order to adjust the pH of the cryopreservation solution to approximately 6.5 to 9.0, preferably to 7.0 to 8.5. Note that the phosphate buffer solution in the present invention refers to sodium chloride, monosodium phosphate (anhydrous), monopotassium phosphate (anhydrous), disodium phosphate (anhydrous), trisodium phosphate (anhydrous), potassium chloride, potassium dihydrogen phosphate (anhydrous), and the like, and it is particularly preferable to use sodium chloride, monosodium phosphate (anhydrous), potassium chloride, or potassium dihydrogen phosphate (anhydrous). The content of the pH adjusting agent in the cryopreservation solution is preferably 0.01 w/v % to 1.0 w/v %, more preferably 0.05 w/v % to 0.5 w/v %.

The cryopreservation solution may contain a thickener. Examples of the thickener can encompass carboxymethyl cellulose (hereinafter, CMC), sodium carboxymethyl cellulose (hereinafter, CMC-Na), organic acid polymers, propylene glycol alginate, sodium alginate, and the like. The thickener is preferably CMC or CMC-Na, particularly preferably CMC-Na. Among the organic acid polymers, sodium polyacrylate is preferable. However, since umbilical cord blood or peripheral blood can be preserved well in the present invention even in a case where the cryopreservation solution contains no thickener, the cryopreservation solution contains no thickener in a preferable embodiment of the cryopreservation method in accordance with the present invention. For use as a cell preparation intended for intravenous administration to a human, the cryopreservation solution desirably contains no thickener.

The cryopreservation solution may or may not contain an animal-derived natural component. Examples of the animal-derived natural component can encompass albumin, a serum, a basal medium, and the like. Examples of the serum can encompass an adult bovine serum, a calf serum, a new born calf serum, a fetal bovine serum, and the like. Examples of the basal medium can encompass RPMI medium, MEM medium, HamF-12 medium, DM-160 medium, and the like. The cryopreservation solution preferably contains no animal-derived natural component. A cryopreservation solution containing no animal-derived natural component is free of a problem of variation in quality from lot to lot of animal-derived natural components, and also allows avoiding (i) a risk that a component contained in the serum and unnecessary for cell preservation, such as various cytokines, growth factors, and hormones, may cause a change in the properties of cells in umbilical cord blood and (ii) an influence of a component which is contained in the basal medium and whose origin is unknown. Accordingly, particularly for clinical use, the cryopreservation solution containing no animal-derived natural component is very useful in that the cryopreservation solution is safely applicable to a living body.

The cryopreservation solution preferably contains no dextran. A cryopreservation solution containing no dextran allows reducing a risk of causing anaphylactic shock and therefore is safely applicable to a living body.

The cryopreservation solution preferably contains no hydroxyethylstarch (HES). A cryopreservation solution containing no hydroxyethylstarch allows reducing a risk of causing anaphylactic shock and therefore is safely applicable to a living body.

The cryopreservation solution is preferably an aqueous solution. The osmotic pressure of the cryopreservation solution is preferably 1000 mOsm or more, more preferably 1000 mOsm to 2700 mOsm so that a performance of the cryopreservation solution as a preservative solution is retained.

Note that the cryopreservation solution has a composition which may be any combination of the specific examples of components listed above, provided that the composition allows the cryopreservation solution to preserve cells sufficiently. As for concentration, it is also possible to select and combine concentrations from the specific examples of concentrations above.

In a preferable example, the cryopreservation solution is an aqueous solution which contains a cryoprotectant and glucose and contains none of an animal-derived natural component, a thickener, dextran, and HES. In a more preferable example, the cryopreservation solution is an aqueous solution which contains DMSO and glucose and contains none of an animal-derived natural component, a thickener, and dextran. In a further more preferable example, the cryopreservation solution is an aqueous solution which contains DMSO in an amount of 6.0 w/v % to 20.0 w/v % and glucose in an amount of 1.0 w/v % to 10.0 w/v % and contains none of an animal-derived natural component, a thickener, dextran, and HES. In a still even more preferable example, the cryopreservation solution is an aqueous solution which contains DMSO in an amount of 10.0 v/v % and glucose in an amount of 3.0 w/v % and contains none of an animal-derived natural component, a thickener, dextran, and HES. In a particularly preferable example, the cryopreservation solution is an aqueous solution which contains only DMSO, glucose, and a pH adjusting agent. In one of the most preferable examples, the cryopreservation solution is an aqueous solution which contains only DMSO, glucose, and a pH adjusting agent, wherein the DMSO is contained in an amount of 6.0 w/v % to 20.0 w/v % and the glucose is contained in an amount of 1.0 w/v % to 10.0 w/v %. In another one of the most preferable examples, the cryopreservation solution is an aqueous solution which contains only DMSO, glucose, and a pH adjusting agent, wherein the DMSO is contained in an amount of 10.0 v/v % and the glucose is contained in an amount of 3.0 w/v %.

In a case where umbilical cord blood or peripheral blood for medical use is cryopreserved, the cryopreservation solution is preferably sterilized. This is because the sterilized cryopreservation solution has less risk of bacterial infection and therefore is applicable more safely to a living body.

Umbilical cord blood or peripheral blood to be cryopreserved may be one from which at least part of red blood cells, preferably all of the red blood cells, has been removed. The removal of the red blood cells allows the umbilical cord blood or peripheral blood to have a reduced volume when frozen, so that a large number of specimens can be preserved easily. The removal of the red blood cells can be performed, for example, by a well-known method.

Further, umbilical cord blood or peripheral blood to be cryopreserved may be one from which at least part of blood plasma has been removed. The removal of the at least part of the blood plasma allows adjusting the volume of the umbilical cord blood or peripheral blood to be mixed with the cryopreservation solution. Further, the removal also allows the umbilical cord blood or peripheral blood to have a reduced volume when frozen, so that a large number of specimens can be preserved easily. The removal of the blood plasma can be performed, for example, by a well-known method.

The cryopreservation solution is mixed with the umbilical cord blood or peripheral blood in a volume ratio of preferably 1:1 to 3:1, more preferably 1:1 to 2:1, and in an example, further more preferably 1:1. Mixing the cryopreservation solution with the umbilical cord blood or peripheral blood in any of the ranges of volume ratio above allows a mixture obtained to have a better cell viability when thawed. The concentration of each component in the cryopreservation solution is adjusted in accordance with the above ratios of mixing. For example, in a case where the cryopreservation solution is mixed with the umbilical cord blood or peripheral blood in a volume ratio of 1:1, the concentration of each component in the cryopreservation solution should be double the concentration of the each component in the mixture.

The total amount of the cryopreservation solution and the umbilical cord blood or peripheral blood is not particularly limited, but may be, for example, 10 mL to 100 mL.

The method of mixing is not particularly limited. The mixing is preferably performed while stirring, from a viewpoint of achieving more homogenous mixture. The temperature at which the mixing is performed is not particularly limited but preferably 10° C. or lower, and it is more preferable that the mixing be performed while icing. Further, the cryopreservation solution is preferably adjusted in advance to the temperature above. By performing the mixing at such a temperature, it is possible to suppress an influence of an increase in temperature of the mixture and, accordingly, further maintain the cell viability.

The mixture obtained in the mixing step is then frozen. Prior to freezing, a sample for examination may be collected and the volume of the mixture may be measured. Further, the mixture may be transferred to a container which is cold resistant (e.g., a freezer bag). While these operations are carried out, the mixture is preferably cooled to 10° C. or lower from a viewpoint of retaining the cell viability.

The freezing step is preferably performed as immediately as possible (e.g., within 30 minutes, preferably within 10 minutes) after the mixing step. Although the rate of cooling is not particularly limited, slow cooling is preferable. The rate of cooling may be, for example, 1° C./min to 3° C./min. In a case of slow cooling, for example, a program freezer or the like may be used. The final temperature at which the freezing is completed is not particularly limited, but preferably −80° C. or lower, more preferably −150° C. or lower, further more preferably −195.8° C. or lower. As the temperature at which the mixture is preserved is lowered, the mixture can be preserved for a longer period and in a better condition. Further, the mixture can be frozen at a temperature of approximately −80° C. and then transferred to an environment at −180° C. to −200° C. (e.g., in liquid nitrogen) so as to be preserved. The mixture is preferably frozen in a cold-resistant container.

Umbilical cord blood or peripheral blood which is cryopreserved by the cryopreservation method in accordance with the present invention has good cell viability when thawed (see Examples described later). From umbilical cord blood or peripheral blood which is cryopreserved by the cryopreservation method in accordance with the present invention, cells can be recovered, for example, with a cell viability of 80% or more, preferably 85% or more, after an elapse of 2 to 3 months from the freezing, relative to a cell viability of 100% in the umbilical cord blood or peripheral blood prior to the freezing. Further, from umbilical cord blood or peripheral blood which is cryopreserved by the cryopreservation method in accordance with the present invention, cells can be recovered, for example, with a cell viability of 80% or more, preferably 85% or more, after an elapse of 1 month, 3 months, 6 months, 1 year, 3 years, 5 years, 10 years, or a longer period (semipermanently) from the freezing, relative to a cell viability of 100% in the umbilical cord blood or peripheral blood prior to the freezing. The viability of CD34-positive cells is particularly good, and can be 90% or more, preferably 95% or more, more preferably 98% or more.

As such, in a case where umbilical cord blood or peripheral blood of a person is cryopreserved by the cryopreservation method in accordance with the present invention, the umbilical cord blood or peripheral blood can be thawed and used in the future when the person or another person receives a medical care. Further, even if there are unknown cells that cannot be separated and collected by current technology, the cryopreservation allows such cells to be effectively used when it becomes possible to isolate the cells in the future. For example, even for a disease which is currently untreatable, cryopreserved umbilical cord blood or peripheral blood can be used in the future when a method for treating the disease is developed. Further, for a congenital genetic disease and the like, cryopreserved umbilical cord blood or peripheral blood can be used as a source of autologous cells for a gene therapy.

Further, umbilical cord blood or peripheral blood cryopreserved by the cryopreservation method in accordance with the present invention, when thawed, has a good TNC (total nucleated cells) recovery rate, a good CD34-positive cell recovery rate, and a good total CFU recovery rate (see the Examples described later). From umbilical cord blood or peripheral blood cryopreserved by the cryopreservation method in accordance with the present invention, cells can be recovered, for example, with a TNC (total nucleated cells) recovery rate of 92.5% or more after an elapse of 2 to 3 months from the freezing, relative to a TNC recovery rate of 100% in the umbilical cord blood or peripheral blood prior to the freezing. From umbilical cord blood or peripheral blood cryopreserved by the cryopreservation method in accordance with the present invention, cells can be recovered, for example, with a CD34-positive cell recovery rate of 67.1% or more after an elapse of 2 to 3 months from the freezing, relative to a CD34-positive cell recovery rate of 100% in the umbilical cord blood or peripheral blood prior to the freezing. From umbilical cord blood or peripheral blood cryopreserved by the cryopreservation method in accordance with the present invention, cells can be recovered, for example, with a total CFU recovery rate of 71.9% or more after an elapse of 2 to 3 months from the freezing, relative to a total CFU recovery rate of 100% in the umbilical cord blood or peripheral blood prior to the freezing.

According to the present invention, umbilical cord blood or peripheral blood can be cryopreserved well without use of dextran. This allows the umbilical cord blood or peripheral blood to be safely applied to a living body when thawed. Further, since the cryopreservation solution is simply mixed with umbilical cord blood or peripheral blood without a need to add anything separately, the umbilical cord blood or peripheral blood can be cryopreserved quickly after being collected.

Note that the present invention encompasses a mixture (composition) of (i) umbilical cord blood or peripheral blood and (ii) the cryopreservation solution which mixture is obtained in the mixing step.

[Method for Thawing Cryopreserved Umbilical Cord Blood or Peripheral Blood]

A method for thawing umbilical cord blood or peripheral blood which has been cryopreserved by the cryopreservation method in accordance with the present invention is not particularly limited. A temperature at which the thawing is performed is not particularly limited, but preferably in a rage of 30° C. to 40° C., more preferably in a range of 37° C. to 40° C. The thawing is preferably carried out quickly, and may be carried out, for example, with use of a constant-temperature water bath which is at 37° C. to 38° C.

The thawed umbilical cord blood or peripheral blood can be used for medical, research, or other purposes. In an example, the thawed umbilical cord blood or peripheral blood may be injected as it is into a living body together with the cryopreservation solution, or injected into a living body after the cryopreservation solution is removed. Alternatively, living cells may be collected from the thawed umbilical cord blood or peripheral blood. The thawed umbilical cord blood, the thawed peripheral blood, or the collected living cells are injected into a living body, for example, by a method such as intravascular administration. As discussed above, the thawed umbilical cord blood or peripheral blood has good cell viability and a good cell recovery rate.

As such, the present invention provides a method for administering umbilical cord blood or peripheral blood which method includes an administration step of administering the thawed umbilical cord blood or peripheral blood to a living body. Further, the present invention provides a method for collecting living cells from umbilical cord blood or peripheral blood which method includes a cell collection step of collecting living cells from the thawed umbilical cord blood or peripheral blood. Further, the present invention provides a method for administering umbilical cord blood or peripheral blood which method includes an administration step of administering, to a living body, living cells collected from the thawed umbilical cord blood or peripheral blood.

In the cell collection step, a method by which the living cells are collected is not particularly limited, and for example, a well-known method for collecting living cells from umbilical cord blood or peripheral blood may be used. The living cells to be collected are not particularly limited, and may be, for example, hematopoietic stem cells or the like. The living cells to be collected are preferably stem cells or precursor cells, more preferably hematopoietic stem cells. Alternatively, the living cells to be collected may be unknown cells which currently cannot be separated. Note that the living cells to be collected are not limited to original cells contained in umbilical cord blood or peripheral blood, and may be cells which were proliferated by a culturing technique (i.e., copies of original cells). The living cells collected can be used for medical, research, and other purposes. In a case where living cells collected are used for a medical purpose, the living cells may be transplanted to the person from whom the living cells collected are derived or to another person.

Further, the present invention encompasses a thawed mixture (composition) of (i) umbilical cord blood or peripheral blood and (ii) the cryopreservation solution.

[Frozen Umbilical Cord Blood or Peripheral Blood, and Method for Producing Same]

A production method in accordance with the present invention for producing frozen umbilical cord blood or frozen peripheral blood includes: a mixing step of mixing a cryopreservation solution with umbilical cord blood or peripheral blood, the cryopreservation solution containing a cryoprotectant and glucose, the umbilical cord blood or peripheral blood containing living cells; and a freezing step of freezing a mixture obtained in the mixing step.

Descriptions for the mixing step and the freezing step are identical to those given in [Method for cryopreserving umbilical cord blood or peripheral blood].

Frozen umbilical cord blood or peripheral blood which is produced by the production method in accordance with the present invention has good cell viability when thawed (see the Examples described later). From frozen umbilical cord blood or peripheral blood in accordance with the present invention, cells can be collected, for example, with a cell viability of 80% or more after an elapse of 2 to 3 months from the freezing, relative to a cell viability of 100% in the umbilical cord blood or peripheral blood prior to the freezing. Further, from umbilical cord blood or peripheral blood which is cryopreserved by the cryopreservation method in accordance with the present invention, cells can be collected, for example, with a cell viability of 80% or more after an elapse of 1 month, 3 months, 6 months, 1 year, 3 years, 5 years, 10 years, or a longer period (semipermanently) from the freezing, relative to a cell viability of 100% in the umbilical cord blood or peripheral blood prior to the freezing.

From the frozen umbilical cord blood or frozen peripheral blood in accordance with the present invention, living cells may be collected by the method of collection described above. The living cells collected can be used for medical, research, and other purposes. The living cells may be, for example, hematopoietic stem cells or the like. Further, the frozen umbilical cord blood or frozen peripheral blood in accordance with the present invention, when thawed, may be injected as it is into a living body or be injected into a living body after the cryopreservation solution is removed.

[Cryopreservation Solution for Cryopreserving Umbilical Cord Blood or Peripheral Blood]

A cryopreservation solution in accordance with the present invention for cryopreserving umbilical cord blood or peripheral blood contains a cryoprotectant and glucose. Descriptions for the cryopreservation solution are basically identical to those given in [Method of cryopreserving umbilical cord blood or peripheral blood].

In an example, the cryoprotectant is contained in the cryopreservation solution in an amount of preferably 6.0 w/v % to 20.0 w/v %, more preferably 10.0 w/v % to 16.0 w/v % or 10.0 v/v % to 16.0 v/v %, and from a viewpoint of cell recovery rate and reduction in the amount of DMSO, more preferably 10.0 v/v %.

In an example, the glucose is contained in the cryopreservation solution in an amount of preferably 0.5 w/v % to 10.0 w/v %, more preferably 1.0 w/v % to 10.0 w/v %, further more preferably 2.0 w/v % to 5.0 w/v %, and particularly preferably 3.0 w/v % to 4.0 w/v %.

[Kit for Cryopreservation]

A kit in accordance with the present invention for cryopreserving umbilical cord blood or peripheral blood includes: the cryopreservation solution described above for cryopreserving umbilical cord blood or peripheral blood; and a container which is cold resistant and capable of containing (i) the cryopreservation solution and (ii) umbilical cord blood or peripheral blood.

The kit in accordance with the present invention is suitably applicable to [Method for cryopreserving umbilical cord blood or peripheral blood] and [Frozen umbilical cord blood or peripheral blood, and method for producing same] which are described above.

The container is not particularly limited, provided that the container is capable of containing the cryopreservation solution and umbilical cord blood or peripheral blood and is cold resistant. The size of the container is not particularly limited, and can be selected as appropriate in accordance with the amount of the umbilical cord blood or peripheral blood to be contained in the container. The size of the container may be, for example, such that the container has a volume of 10 mL to 100 mL, preferably 20 mL to 30 mL. The degree of cold resistance is not particularly limited, provided that the container can tolerate a temperature at which the umbilical cord blood or peripheral blood is preserved. For example, the container is preferably made of a material capable of tolerating a temperature of −80° C., more preferably a material capable of tolerating a temperature of −200° C. Examples of such a container encompass a container made of a synthetic resin such as polyethylene, polypropylene, polystyrene, polyethylene terephthalate, polycarbonate, fluorinated ethylene propylene, and the like. The container is preferably sealable, and the inside of the container is preferably sterilized.

The kit in accordance with the present invention may further include an instruction manual for the kit. The instruction manual for the kit has recorded therein the content of the cryopreservation method in accordance with the present invention described above in the section [Method for cryopreserving umbilical cord blood or peripheral blood] and/or the content of the production method in accordance with the present invention described above in the section [Frozen umbilical cord blood or peripheral blood, and method for producing same]. Further, the instruction manual for the kit may have recorded therein an instruction to use the cryopreservation solution so as to achieve a predetermined final concentration.

[Conclusion]

As described above, a cryopreservation method in accordance with the present invention is a cryopreservation method for cryopreserving umbilical cord blood or peripheral blood, including: a mixing step of mixing a cryopreservation solution with umbilical cord blood or peripheral blood, the cryopreservation solution containing a cryoprotectant and glucose; and a freezing step of freezing a mixture obtained in the mixing step.

The cryopreservation method in accordance with the present invention is preferably arranged such that the cryopreservation solution contains no thickener.

The cryopreservation method in accordance with the present invention is preferably arranged such that the cryopreservation solution contains no animal-derived natural component.

The cryopreservation method in accordance with the present invention is preferably arranged such that the cryoprotectant is dimethyl sulfoxide.

The cryopreservation method in accordance with the present invention is preferably arranged such that the mixture contains the cryoprotectant in an amount of 3.0 w/v % to 10.0 w/v % and the glucose in an amount of 0.25 w/v % to 5.0 w/v %.

The cryopreservation method in accordance with the present invention is preferably arranged such that in the mixing step, the cryopreservation solution is mixed with the umbilical cord blood or the peripheral blood in a ratio of 1:1 to 3:1.

The cryopreservation method in accordance with the present invention is preferably arranged such that the umbilical cord blood or the peripheral blood is one from which at least part of red blood cells has been removed.

The cryopreservation method in accordance with the present invention is preferably arranged such that the umbilical cord blood or the peripheral blood is derived from a human.

A production method in accordance with the present invention for producing frozen umbilical cord blood or frozen peripheral blood is a production method for producing frozen umbilical cord blood or frozen peripheral blood, including: a mixing step of mixing a cryopreservation solution with umbilical cord blood or peripheral blood, the cryopreservation solution containing a cryoprotectant and glucose, the umbilical cord blood or peripheral blood containing living cells; and a freezing step of freezing a mixture obtained in the mixing step.

The present invention also provides frozen umbilical cord blood or frozen peripheral blood, produced by the production method above.

A cryopreservation solution in accordance with the present invention for cryopreserving umbilical cord blood or peripheral blood contains a cryoprotectant and glucose.

A kit in accordance with the present invention is a kit for cryopreserving umbilical cord blood or peripheral blood, including: the cryopreservation solution above for cryopreserving umbilical cord blood or peripheral blood; and a container which is cold resistant and capable of containing (i) the cryopreservation solution and (ii) umbilical cord blood or peripheral blood.

The embodiments of the present invention will be described in further detail via the following Examples. Needless to say, the present invention is not limited to the Examples, and details of the present invention can be realized in various manners. Further, the present invention is not limited to the description of the embodiments above, but may be altered in various ways within the scope of the appended Claims. An embodiment based on a proper combination of technical means disclosed in different embodiments is encompassed in the technical scope of the present invention. Furthermore, all the documents described herein are incorporated herein by reference in their entirety.

EXAMPLES

Example 1

[Preparation of Cryopreservation Solutions]
Cryopreservation Solution A (Example):
As a cryopreservation solution A, a sterilized aqueous solution containing 10.0 v/v % (11.0 w/v %) of DMSO, 3.0 w/v % of glucose, and a suitable amount of a pH adjusting agent was prepared.
Cryopreservation Solution B (Comparative Example):
As a cryopreservation solution B, a sterilized aqueous solution containing 50.0% v/v (55 w/v %) of DMSO and 5.0 w/v % of dextran (Dex40) was prepared.
[Treatment of Umbilical Cord Blood]
(1. Addition of HES)
⅕ of the amount of a raw material umbilical cord blood was calculated as the volume of hydroxyethylstarch (HES). Then, inside a safety cabinet, an operation adaptor was inserted into a bag for the raw material umbilical cord blood. The required amount of HES was added using a syringe. The raw material umbilical cord blood and the HES were sufficiently mixed.
(2. Separation of Cells)
A tube of the bag for the raw material umbilical cord blood was clamped, and then connected with a separation bag for cells with use of a sterile connecting device (TSCD). The bag for the raw material umbilical cord blood was set on a separation stand and left to stand until there was a clear boundary between red blood cells and blood plasma (for approximately 60 to 90 minutes). When the boundary became clear, the tube was unclamped and the blood plasma and a white blood cell layer (buffy coat) were transferred to the separation bag for cells. At this time, up to 3 g of a red blood cell layer was allowed to enter the separation bag for cells. The tube was clamped, and then the bag for the raw material umbilical cord blood and the separation bag for cells were sealed with use of a tube sealer and detached from each other.
(3. Removal of Blood Plasma)
A tip of a tube of a separation bag for blood plasma removal was clamped over a package. Then, the package was opened, and the tube was sealed at a position closer to the bag than the clamped portion (the sterility of the bag was maintained until TSCD connection). With confirmation of the separation bag for cells, the separation bag for blood plasma removal was marked or labeled with an umbilical cord blood control number, and it was confirmed that the separation bag for cells and the separation bag for blood plasma removal matched in umbilical cord blood control number. A tube of the separation bag for cells was clamped, and then connected with the separation bag for blood plasma removal with use of a sterile connecting device (TSCD). The separation bag for cells and the separation bag for blood plasma removal thus connected with each other were inserted upright in a bucket of a high capacity centrifuge. Centrifugation was conducted with a centrifugation condition set to 400×G and 10 minutes. Upon completion of the centrifugation, the separation bag for cells was set on a separation stand. The clamp was removed, and blood plasma was transferred into the separation bag for blood plasma removal. In doing so, the amount of the blood plasma was adjusted so that concentrated umbilical cord blood in the separation bag for cells had a volume of approximately 13.0 mL in a case of mixing the concentrated umbilical cord blood with the cryopreservation solution A, or a volume of 23.4 mL in a case of mixing the concentrated umbilical cord blood with the cryopreservation solution B. Tubing between the separation bag for cells and the separation bag for blood plasma removal was sealed with use of a tube sealer, and the separation bag for cells and the separation bag for blood plasma removal were detached from each other. The weight of the separation bag for cells was measured and recorded.
(4. Addition of Cryopreservation Solution)

The separation bag for cells was set on an agitator so as to be cooled by a refrigerating agent. The injection rate (flow rate) of a syringe pump for the cryopreservation solution A was set to 120 mL/hr, and the setting was confirmed (level 4). The injection rate (flow rate) of a syringe pump for the cryopreservation solution B was set to 20 mL/hr, and the setting was confirmed. A required amount of the cryopreservation solution A or the cryopreservation solution B which had been cooled in advance was dispensed into the syringe. The syringe into which the cryopreservation solution A or the cryopreservation solution B was thus dispensed was fitted with a winged intravenous needle and attached to the syringe pump. The winged intravenous needle was inserted into an operation adaptor, and the cryopreservation solution was injected while being cooled and stirred. At this time, the amounts of the cryopreservation solution A and the cryopreservation solution B injected were 13.0 mL and 4.4 mL, respectively. As a result, the cryopreservation solution A when frozen had a final concentration of 5.0 v/v % of DMSO and 1.5 w/v % of glucose, and the cryopreservation solution B when frozen had a final concentration of 8.0 v/v % of DMSO and 0.8 w/v % of dextran (Dex40).
(5. Dispensing of Specimen for Cell Count Measurement)

With confirmation of the umbilical cord blood control number on the separation bag for cells, a tube for specimen was labeled. An operation adaptor was inserted into the separation bag for cells, the cells inside the separation bag for cells were suspended uniformly, and 0.5 mL of the umbilical cord blood, which was unfrozen, was dispensed into an examination tube. Further, 0.5 mL of the unfrozen umbilical cord blood was dispensed as a specimen for a sterility test.
(6. Transfer to Freezer Bag)

A plastic needle of a freezer bag was inserted into a port of the separation bag for cells, and the entire unfrozen umbilical cord blood was transferred into the freezer bag. The tube of the freezer bag was filled with the unfrozen umbilical cord blood, so that a segment was produced. The final weight of the freezer bag was measured, and the number of an electronic scale number used and the final weight were recorded. The unfrozen umbilical cord blood was cooled with a refrigerating agent until a start of a freezing treatment. Note that the freezing was started within 30 minutes from the completion of the addition of the cryopreservation solution A.
(7. Freezing)

It was confirmed that the freezer bag, a canister, the segment, and an operation recording sheet match in umbilical cord blood control number, and the freezer bag was stored in the canister. With use of a program freezer, the freezing treatment was conducted at a cooling rate of 1° C./min to 3° C./min. At each freezing step, a change in temperature when freezing occurred was measured and recorded. Upon completion of the freezing treatment, the freezer bag was immediately transferred into a gas phase of a liquid nitrogen tank.

[Thawing of Cryopreserved Umbilical Cord Blood]

The freezer bag containing umbilical cord blood which had been cryopreserved for 2 to 3 months was put in a constant-temperature water bath at 35° C. to 37° C. so as to thaw the umbilical cord blood. The umbilical cord blood thus thawed was iced until a start of each test.

[Examinations Related to Hematopoietic Cells]
(1. Examination of Nucleated Cells)

Examination of WBC (white blood cells) and NRBC (nucleated red blood cells) was conducted with respect to unfrozen umbilical cord blood and thawed umbilical cord blood. The examination apparatus used was an automated blood cell counter Sysmex XE-2100, which was based on a flow cytometry technique using a semiconductor laser. The reagents used (Sysmex Corporation) are shown in Table 1.

TABLE 1

| Reagent name | | Dose/specimen |
|---|---|---|
| Cellpack (II) | EPK | approx. 30 mL |
| SE sheath (II) | ESE | approx. 2.1 mL |
| Stromatolyser FB (II) | FBT | approx. 1.8 mL |
| Stromatolyser 4DL | FFD | approx. 1.8 mL |
| Stromatolyser 4DS | FFS | approx. 18 μL |
| Stromatolyser NR hemolytic agent | SNR | approx. 1.8 mL |
| Stromatolyser NR dye | SNR | approx. 18 μL |
| Sulfolyser | SLS | approx. 0.5 mL |
| Stromatolyser IM | SIM | approx. 3.1 mL |
| RET-search (II) diluent | RED | approx. 1.8 mL |
| RET-search (II) dye | RED | approx. 18 μL |

The specimen was diluted as appropriate using Cellpack, and was stirred sufficiently. The measurement was conducted in a manual mode. The examination data was used to calculate a nucleated cell count concentration [(WBC+ NRBC)×dilution rate]. The nucleated cell count concentration was used to calculate a TNC (total nucleated cells) recovery rate.
(2. Examination of CD34-Positive Cell Count and Cell Viability)

Examination of CD34-positive cell count and cell viability was conducted with respect to unfrozen umbilical cord blood and thawed umbilical cord blood. The examination apparatus used was a flow cytometer (hereinafter, FCM) Cytomics FC500 (manufactured by Beckman Coulter, Inc.), which was based on a flow cytometry technique using a semiconductor laser. Further, as analysis software, stemCXP software (manufactured by Beckman Coulter, Inc.) was used. The measurement was conducted with use of a kit for measuring CD34-positive cell count (StemKit, Beckman Coulter, Inc., A15573). Other reagents etc. used are shown in Table 2.

TABLE 2

| Reagent name | |
|---|---|
| IsoFlow sheath fluid | Beckman 8599600 |
| Clenz (device cleaning fluid) | Beckman 8546930 |
| Flow check | Beckman 6605359 |

The amount and specimen number of each specimen were confirmed, and the specimen was diluted with 2% FBS PBS (−). Three tubes (manufactured by Beckman Coulter, Inc., A26428) for the specimen were prepared and marked with the specimen number and SEQ numbers (1 to 3). To each of the tubes 1 and 2, 20 μL of 7-AAD and 20 μL of CD45-FITC/CD34-PE were added. To the tube 3, 20 μL of 7-AAD and 20 μL of CD45-FITC were added. To each of the tubes 1 to 3, 100 μL of the specimen was added and mixed sufficiently. A mixture thus obtained was left to react in a dark place at room temperature for 20 minutes. A hemolytic agent (NH₄Cl Lysing Solution) was diluted 10-fold with purified water, and added in an amount of 2 mL to each tube (the hemolytic agent was prepared in situ) so as to be mixed sufficiently. A mixture thus obtained was left to react in a dark place at room temperature for 10 minutes.

The CXP program was activated, and setting of a measurement panel was conducted. The specimen number etc. were inputted, and the measurement was started. Upon completion of the measurement, data were confirmed and, if necessary, Gate was corrected by performing a Listmode playback.

On the basis of the analytical data, the concentration and cell count of CD34-positive cells were calculated. In the case of the thawed umbilical cord blood, cell viability was also calculated.

(3. Examination of Colony Forming Cell (CFU) Count)

Examination of CFU-GM count and total CFU count was conducted with respect to the unfrozen umbilical cord blood and the thawed umbilical cord blood. The reagents (STEM-CELL Technologies) are shown in Table 3.

TABLE 3

| Reagent name | Dose/specimen |
| --- | --- |
| Medium for CFU: MethoCult H4034 Optimum (st04044V) | approx. 4 mL |
| For dilution of specimen: 2% FBS-containing IMDM | suitable amount |
| For wetting petri dish: Sterilized distilled water | approx. 6 mL |

MethoCult H4034 Optimum (st04044V) which had been cryopreserved (−15° C. to −25° C.) (approximately 4 mL) was taken out of a freezer, and thawed at or below room temperature. The specimen was diluted with a 2% FBS-containing IMDM medium so as to achieve a nucleated cell concentration of approximately 400 cells/µL, and was stirred sufficiently. To 4 mL of the thawed MethoCult H4034 Optimum (st04044V), 400 µL of the specimen with the nucleated cell concentration thus adjusted was added and stirred intensively with a mixer. A mixture thus obtained was left to stand for approximately 5 minutes until large air bubbles began to rise.

With use of a syringe and needle for methylcellulose, 1.1 mL of the specimen mixed with the medium was dispensed into each of three 35 mm petri dishes. The three 35 mm petri dishes were stored in a 90 mm petri dish, together with a 35 mm petri dish for distilled water, which 35 mm petri dish contained approximately 3 mL of sterilized distilled water. The 90 mm petri dish was put in a CO₂ incubator, and cells were cultured under the conditions of 37° C., 5% CO₂, and 100% humidity for 12 to 15 days.

After the culture, a CFU count was counted under an inverted microscope (TS100 (manufactured by Nikon) or IX71-PH (manufactured by Olympus)). On the basis of the counted values, a CFU-GM count and a total CFU count were calculated. With use of the values thus obtained, a CFU-GM recovery rate and a total CFU recovery rate were calculated.

(4. Results)

Results of the examinations related to hematopoietic cells are collectively shown in Table 4 (unit: %).

TABLE 4

|  | Cryopreservation solution A (n = 11) | Cryopreservation solution B (n = 11) |
| --- | --- | --- |
| TNC recovery rate | 101.9 ± 6.9 | 101.0 ± 6.4 |
| CD34-positive cell recovery rate | 95.0 ± 14.8 $p<0.01$ | 80.0 ± 8.8 |
| Total CFU recovery | 95.7 ± 16.8 | 85.7 ± 12.8 |
| CFU GM recovery rate | 92.3 ± 21.8 | 92.7 ± 17.9 |
| Living cell viability (fluorescent microscope) AO/EB | 86.8 ± 2.9 | 88.6 ± 7.9 |
| Living cell viability (Flow) CD45 site | 74.0 ± 6.1 | 71.4 ± 9.8 |
| Living cell viability (Flow) CD34 site | 99.4 ± 0.7 | 99.1 ± 0.8 |

Example 2

[Preparation of Cryopreservation Solutions]

Cryopreservation Solution C (Example):

As a cryopreservation solution C, a sterilized aqueous solution containing 16.0 v/v % (17.6 w/v %) of DMSO, 3.0 w/v % of glucose, and a suitable amount of a pH adjusting agent was prepared.

Cryopreservation Solution B (Comparative Example):

As a cryopreservation solution B, a sterilized aqueous solution containing 50.0% v/v (55 w/v %) of DMSO and 5.0 w/v % of dextran (Dex40) was prepared.

[Treatment of Umbilical Cord Blood]

The treatment of umbilical cord blood was conducted in accordance with a similar procedure as in Example 1. Note that the cryopreservation solution C when frozen had a final concentration of 8.0 v/v % of DMSO and 1.5 w/v % of glucose, and the cryopreservation solution B when frozen had a final concentration of 8.0 v/v % of DMSO and 0.8 w/v % of dextran (Dex40).

[Thawing of Cryopreserved Umbilical Cord Blood]

The freezer bag containing umbilical cord blood which had been cryopreserved for 2 months was put in a constant-temperature water bath at 35° C. to 37° C. so as to thaw the umbilical cord blood. The umbilical cord blood thus thawed was iced until a start of each test.

[Examinations Related to Hematopoietic Cells]

Examinations related to hematopoietic cells were conducted in a similar manner to Example 1.

(Results)

Results of the examinations related to hematopoietic cells are collectively shown in Table 5 (unit: %). Table 5 also shows results which were recalculated from the results in Table 4 of Example 1 in consideration of a difference between the cryopreservation solution A and the cryopreservation solution B in timing of collecting umbilical cord blood. Note that the results of the cryopreservation solution C in Table 5 were calculated in consideration of a timing of collecting umbilical cord blood. As for the cryopreservation solution B, results obtained in Example 1 and results obtained in Example 2 are merged in Table 5, since the same evaluation method was employed between Examples 1 and 2.

TABLE 5

|  | Cryo-preservation solution A (n = 11) | Cryo-preservation solution B (n = 21) | Cryo-preservation solution C (n = 15) |
|---|---|---|---|
| TNC recovery rate | 101.2 ± 7.1 | 100.0 ± 7.1 | 99.0 ± 4.1 |
| CD34-positive cell recovery rate | 96.5 ± 13.1 | 93.0 ± 9.1 $p<0.01$ | 86.9 ± 9.2 |
| Total CFU recovery | 98.3 ± 19.1 | 95.6 ± 19.5 | 94.3 ± 18.0 |
| CFU GM recovery rate | 92.5 ± 23.7 | 99.7 ± 23.9 | 97.0 ± 22.3 |
| Living cell viability (fluorescent microscope) AO/EB | 86.8 ± 2.9 | 85.7 ± 7.6 | 83.2 ± 2.8 |
| Living cell viability (Flow) CD45 site | 74.0 ± 6.1 | 75.2 ± 9.7 $p<0.001$ | 84.2 ± 2.6 |
| Living cell viability (Flow) CD34 site | 89.4 ± 0.7 $p<0.01$ | 98.1 ± 1.7 | 98.8 ± 1.1 |

TABLE 6

|  | Cryopreservation solution A (n = 10) | Cryopreservation solution C (n = 10) |
|---|---|---|
| TNC recovery rate | 100.9 ± 8.3 $p<0.05$ | 97.6 ± 5.9 |
| CD34-positive cell recovery rate | 92.9 ± 11.1 $p<0.05$ | 83.2 ± 15.4 |
| Total CFU recovery | 87.8 ± 28.2 | 82.0 ± 20.4 |
| CFU GM recovery rate | 87.9 ± 27.1 | 76.8 ± 25,0 |
| Living cell viability (fluorescent microscope) AO/EB | 88.2 ± 4.9 | 86.2 ± 6.5 |
| Living cell viability (Flow) CD45 site | 75.9 ± 5.8 $p<0.0001$ | 82.8 ± 5.2 |
| Living cell viability (Flow) CD34 site | 98.3 ± 3.7 | 98.5 ± 1.0 |

Example 3

With use of a same specimen, a comparative experiment of cryopreservation of umbilical cord blood was conducted.
[Preparation of Cryopreservation Solutions]
Cryopreservation Solution A (Example):

As a cryopreservation solution A, a sterilized aqueous solution containing 10.0 v/v % (11.0 w/v %) of DMSO, 3.0 w/v % of glucose, and a suitable amount of a pH adjusting agent was prepared.
Cryopreservation Solution C (Example):

As a cryopreservation solution C, a sterilized aqueous solution containing 16.0 v/v % (17.6 w/v %) of DMSO, 3.0 w/v % of glucose, and a suitable amount of a pH adjusting agent was prepared.
[Treatment of Umbilical Cord Blood]

Red blood cells were removed in accordance with a similar procedure as in Example 1, and centrifugal concentration was conducted until the umbilical cord blood had a volume of 26.5 mL. From the umbilical cord blood thus concentrated, 0.5 mL was collected as a sample of unfrozen umbilical cord blood, and the remaining portion was divided in half (13.0 mL). Each half was mixed with 13.0 mL of the cryopreservation solution A or the cryopreservation solution C in accordance with a similar procedure as in Example 1, and then cryopreserved in accordance with a similar procedure as in Example 1. The cryopreservation solution A when frozen had a final concentration of 5.0 v/v % of DMSO and 1.5 w/v % of glucose, and the cryopreservation solution C when frozen had a final concentration of 8.0 v/v % of DMSO and 1.5 w/v % of glucose.
[Thawing of Cryopreserved Umbilical Cord Blood]

The freezer bag containing umbilical cord blood which had been cryopreserved for 2 months was put in a constant-temperature water bath at 35° C. to 37° C. so as to thaw the umbilical cord blood. The umbilical cord blood thus thawed was iced until a start of each test.
[Examinations Related to Hematopoietic Cells]

Examinations related to hematopoietic cells were conducted in a similar manner to Example 1.
(Results)

Results of the examinations related to hematopoietic cells are collectively shown in Table 6 (unit: %).

As compared with the cryopreservation solution C, the cryopreservation solution A had higher cell recovery rates. Also from a viewpoint of reduction in the amount of transfused DMSO, the cryopreservation solution A is considered preferable to the cryopreservation solution C.

INDUSTRIAL APPLICABILITY

The present invention is applicable to cryopreservation of umbilical cord blood and peripheral blood for medical, research, and other purposes.

The invention claimed is:

1. A method for administering umbilical cord blood or peripheral blood, comprising:
   a cryopreservation step of cryopreserving a mixture of (i) a cryopreservation solution and (ii) umbilical cord blood or peripheral blood to obtain cryopreserved material;
   a thawing step of thawing the cryopreserved material obtained in the cryopreservation step; and
   an administration step of administering, to a living body, the umbilical cord blood or peripheral blood and the cryopreservation solution that are thawed in the thawing step,
   the cryopreservation solution containing dimethyl sulfoxide and glucose, and containing no thickener and no dextran,
   wherein the umbilical cord blood or the peripheral blood contains stem cells, and
   wherein the mixture contains the dimethyl sulfoxide in an amount of 3.0 w/v % to 5.0 w/v % and the glucose in an amount of 1.5 w/v %.

2. The method as set forth in claim 1, wherein the cryopreservation solution contains no animal-derived natural component.

3. The method as set forth in claim 1, wherein in the mixture, the volume ratio of the cryopreservation solution to the umbilical cord blood or peripheral blood is 1:1 to 3:1.

4. The method as set forth in claim 1, wherein the umbilical cord blood or the peripheral blood is one from which at least part of red blood cells has been removed.

5. The method as set forth in claim 1, wherein the umbilical cord blood or the peripheral blood is derived from a human.

6. The method as set forth in claim 1, wherein the administration is carried out with respect to a human.

7. The method as set forth in claim 1, wherein the living body is a human in need of a transplant of cells contained in the umbilical cord blood or peripheral blood.

* * * * *